(12) United States Patent
Van Herpen et al.

(10) Patent No.: US 7,560,708 B2
(45) Date of Patent: Jul. 14, 2009

(54) LUMINESCENCE SENSOR USING MULTI-LAYER SUBSTRATE STRUCTURE

(75) Inventors: Maarten Marinus Johannes Wilhelm Van Herpen, Eindhoven (NL); Derk Jan Wilfred Klunder, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1 day.

(21) Appl. No.: 11/995,696

(22) PCT Filed: Jul. 7, 2006

(86) PCT No.: PCT/IB2006/052300

§ 371 (c)(1),
(2), (4) Date: Jan. 15, 2008

(87) PCT Pub. No.: WO2007/010428

PCT Pub. Date: Jan. 25, 2007

(65) Prior Publication Data

US 2008/0197292 A1    Aug. 21, 2008

(30) Foreign Application Priority Data

Jul. 18, 2005    (EP)  .................................. 05106551

(51) Int. Cl.
*G01J 1/58* (2006.01)
(52) U.S. Cl. .................................. 250/458.1; 435/287.2
(58) Field of Classification Search ............... 250/458.1; 435/287.2
See application file for complete search history.

(56) References Cited

U.S. PATENT DOCUMENTS

| 5,418,136 | A  | * | 5/1995 | Miller et al. .................... 435/5 |
| 2002/0192680 | A1 | * | 12/2002 | Chan et al. ...................... 435/6 |
| 2003/0174992 | A1 |  | 9/2003 | Levene et al. |
| 2004/0029303 | A1 | * | 2/2004 | Hart et al. ...................... 438/16 |
| 2005/0196876 | A1 | * | 9/2005 | Chan et al. .................. 436/518 |
| 2006/0051976 | A1 | * | 3/2006 | Guttman et al. ............. 438/778 |

FOREIGN PATENT DOCUMENTS

EP          0009757          2/2000

OTHER PUBLICATIONS

By Taitt C.R. et al.; Entitled: "Evanescent Wave Fluorescence Biosensors" Biosensors & Bioelectronics, Elsevier Science Publishers, Barking, GB, vol. 20, No. 12, Jun. 15, 2005, pp. 2470-2487, XP004861161 ISSN: 0956-5663.

* cited by examiner

*Primary Examiner*—David P Porta
*Assistant Examiner*—Marcus H Taningco

(57) ABSTRACT

The present invention provides a luminescence sensor (2), such as e.g. a luminescence biosensor, comprising a multi-layer structure. The multi-layer structure comprises at least a first layer (2a) formed of a first material and a second layer (2b) formed of a second material. The first material has a first binding capacity towards luminophores and the second material has a second binding capacity towards luminophores, the first binding capacity being different from the second binding capacity. The luminescence sensor (2) according to the present invention shows a high sensitivity because it provides preferred binding sites for luminophores at locations where the combined excitation and detection efficiency is the highest.

17 Claims, 4 Drawing Sheets

LUMINESCENCE SENSOR USING MULTI-LAYER SUBSTRATE STRUCTURE

The present invention relates to luminescence sensors, such as luminescence biosensors or luminescence chemical sensors, comprising a multi-layer substrate structure, such as e.g. a multi-layer wire grid, and providing binding sites at specific positions of said multi-layer substrate structure, e.g. wire grid. The present invention also relates to a method for the manufacturing of such luminescence sensors. The luminescence sensors according to the present invention show a high sensitivity.

Sensors are widely used for measuring a physical attribute or a physical event. They output a functional reading of that measurement as an electrical, optical or auditory signal and can output a digital signal, for example. Such a signal is data that can be transformed by other devices into useful information. A particular example of a sensor is a biosensor. Biosensors are devices that detect the presence of (i.e. qualitative) or measure a certain amount (i.e. quantitative) of target entities such as e.g., but not limited thereto, molecules, proteins, viruses, bacteria, protozoa, cell components, cell membranes, spores, nucleotides such as DNA, RNA, etc. in a fluid, such as for example blood, serum, plasma, saliva, . . . . The target molecules also are called the "analyte". In almost all cases, a biosensor uses a surface that comprises specific recognition elements for capturing the analyte. Therefore, the surface of the sensor device may be modified by attaching specific molecules to it, which are suitable to bind the target molecules which are present in the fluid.

For optimal binding efficiency of the analyte to the specific molecules, large surface areas and short diffusion lengths are highly favourable. Therefore, micro- or nano-porous substrates (membranes) have been proposed as biosensor substrates that combine a large area with rapid binding kinetics. Especially, when the analyte concentration is low (e.g. below 1 nM, or below 1 pM) the diffusion kinetics play an important role in the total performance of a biosensor assay.

The amount of bound analyte may be detected by fluorescence. In this case the analyte itself may carry a fluorescent label, or alternatively an additional incubation with a fluorescently labelled second recognition element may be performed.

Detecting the amount of bound analyte can be hampered by several factors, such as scattering, bleaching of the luminophore, background fluorescence of the substrate and incomplete removal of excitation light. Moreover, to be able to distinguish between bound labels and labels in solution it is necessary to perform a washing step (or steps) to remove unbound labels.

In luminescence sensors with sub-wavelength spatial resolution operating inside a fluid light is reflecting on sub-wavelength apertures or slits, because they are too small to be seen by the light. This yields an evanescent field within the apertures or slits, which is used for exciting luminophores present there. The luminescence sensor is irradiated with excitation radiation from a first side of the sensor. Luminescence that is generated may exit the apertures or slits of the sensor at the side opposite to the first side, i.e. opposite to the side at which the sensor is irradiated, and is detected there, in that way separating excitation and luminescence radiation. Background luminescence generated on the excitation side of the apertures or slits is also suppressed by this (reflection) effect.

However, luminescence sensors comprising slits or apertures may have a problem of determining the specific locations where the luminophores should preferably bind to the surface. In other words, it is difficult to locate or provide preferred binding sites at locations where the combined excitation and detection efficiency is the highest, and thus it is difficult to obtain a high sensitivity.

It is an object of the present invention to provide an improved luminescence sensor, such as a luminescence biosensor or luminescence chemical sensor, with an optical output, as well as a method for the manufacturing of such a luminescence sensor. An advantage of the present invention is a luminescence sensor with a high sensitivity.

The above objective is accomplished by a method and device according to the present invention.

Particular and preferred aspects of the invention are set out in the accompanying independent and dependent claims. Features from the dependent claims may be combined with features of the independent claims and with features of other dependent claims as appropriate and not merely as explicitly set out in the claims.

The present invention provides a luminescence sensor, such as e.g. a luminescence biosensor or luminescence chemical sensor, comprising a first porous multi-layer substrate structure with apertures such as e.g. holes, pinholes, gaps, slits or other openings formed in the substrate in which the multi-layer substrate structure comprises at least one first layer formed of a first material and at least one second layer formed of a second material, wherein the first material shows a first binding capacity toward luminophores present in the apertures and the second material shows a second binding capacity toward luminophores, e.g. fluorophores, present in the apertures, the first binding capacity being higher than the second binding capacity.

An advantage of the sensor according to the invention is that it provides preferred binding sites at locations where the combined excitation and detection efficiency is the highest and thus shows a high efficiency.

Luminophores, e.g. fluorophores, may preferably be positioned closest to an excitation radiation source irradiating the sensor and being positioned at a first side of the sensor because the excitation efficiency is the highest at that position. In embodiments according to the invention, detection of luminescence radiation may be performed at a second side of the sensor opposite to the first side. However, in other, but less preferred, embodiments, detection of luminescence radiation may also be performed at the same first side of the sensor.

According to an embodiment of the invention, the multi-layer substrate structure may comprise slits and one first layer and one second layer.

In other embodiments of the invention, the multi-layer substrate structure may comprise pinholes and one first and one second layer.

According to embodiments of the invention, the first layer may be positioned on top of the second layer and may be closest to a side of the sensor where an excitation radiation source is positioned for irradiating the sensor.

According to an embodiment of the invention, the multi-layer substrate structure may comprise a further second layer, wherein the first layer is sandwiched in between the second layer and the further second layer. The further second layer may be formed of a material which shows a lower binding capacity toward luminophores than the material of the first layer.

In embodiments of the invention, the sensor may furthermore comprise a second substrate structure formed of a material which shows a binding capacity toward luminophores, e.g. fluorophores, which is lower than the first binding capacity of the first layer, and being positioned on top of the first multi-layer substrate structure. Preferably, the material of the second substrate structure may show substantially no binding capacity toward luminophores, e.g. fluorophores.

According to an embodiment of the invention, the first multi-layer substrate structure may lie in a first plane and may have slits running in a first direction and the second substrate structure may lie in a second plane and may have slits running in a second direction. The first plane may be substantially parallel to the second plane and the first direction may be substantially perpendicular to the second direction.

According to embodiments of the invention, the luminescence sensor may be a luminescence biosensor or luminescence chemical sensor. More specifically, the luminescence sensor may be a fluorescence sensor, such as a fluorescence biosensor.

In embodiments according to the invention, the apertures present in the multi-layer substrate structure of the sensor may have sub-wavelength dimensions.

A luminescence sensor according to embodiments of the present invention may furthermore comprise an excitation radiation source for irradiating the sensor, and a detector for detecting generated luminescence radiation, wherein said excitation radiation source is positioned at a first side of the sensor and said detector is positioned at a second side of the sensor, the first and second side being opposite to each other. This set-up may be used for performing transmission measurements. Alternatively, the excitation radiation source and the detector may be positioned at a same side of the sensor. This set-up may be used for performing reflection measurements.

According to a further embodiment of the invention, the multi-layer substrate structure as described in the above embodiments, may furthermore comprise at least one layer with a chemical composition such that, when the luminescence sensor is in contact with a fluid to be examined, no reaction takes place between the luminescence sensor and the fluid the sensor is in contact with.

The present invention furthermore provides a method for the manufacturing of a luminescence sensor, e.g. luminescence biosensor or luminescence chemical sensor, for the detection of luminophores, e.g. fluorophores, the sensor comprising a first multi-layer substrate structure. The method comprises:

providing at least one first layer formed of a first material that has a first binding capacity toward luminophores, providing on the at least one first layer at least one second layer formed of a second material that has a second binding capacity, lower than the first binding capacity, toward luminophores, and providing at least one aperture through the at least one first layer and the at least one second layer.

The method according to the present invention leads to a luminescence sensor, e.g. luminescence biosensor or luminescence chemical sensor, which provides preferred binding sites at locations where the combined excitation and detection efficiency is the highest and thus shows a high efficiency.

According to embodiments of the invention, providing at least one first layer and providing at least one second layer may comprise providing a first layer and two second layers such that the first layer is sandwiched in between the two second layers.

The first multi-layer substrate structure may comprise slits lying in a first plane and running in a first direction. According to embodiments of the invention, the method may furthermore comprise providing on top of the first multi-layer substrate structure a second substrate structure lying in a second plane and having slits running in a second direction, such that the first plane is substantially parallel with the second plane and the first direction is substantially perpendicular to the second direction.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
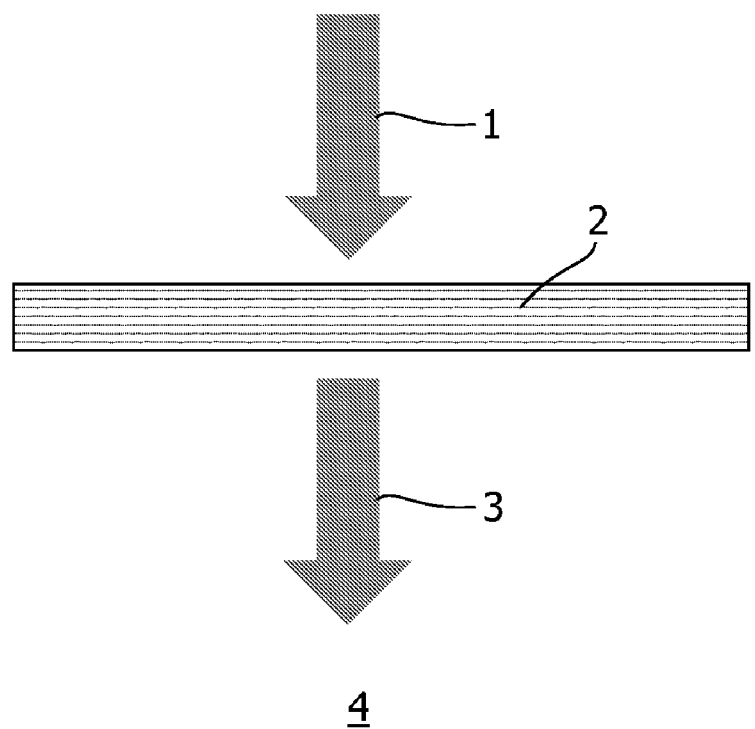
FIG. 1 illustrates the basic principle of a luminescence sensor according to embodiments of the present invention, for use in transmission measurements.

In the different figures, the same reference signs refer to the same or analogous elements.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

The present invention provides a luminescence sensor, e.g. a luminescence biosensor or a luminescence chemical sensor, having a porous multi-layer substrate structure, and a method for the manufacturing of such a luminescence sensor. The discussion hereinafter will be made with reference to embodiments having a substrate comprising a slit structure and hence forming a porous substrate. However, it has to be understood that the invention is not limited to this but may also be used in case of aperture structures, such as e.g. holes, pinholes, gaps or other openings formed in the substrate. The main requirement for the substrate material is that it is not transparent for excitation radiation, i.e. that the material between the apertures or slits is not transparent for the excitation radiation. The sensor device according to the present invention comprises at least one aperture or slit which is to be filled with a medium. The sensor does not need to be immersed in the medium; the medium may also e.g. be sprayed over the sensor and into the at least one aperture or slit, or the apertures or slits may be filled with the medium in any other suitable way, e.g. by means of a micropipette in case of a liquid medium. The medium which fills the slits may be a liquid or a gas, but may also be vacuum comprising at least one luminescent particle to be detected.

The luminescence sensor, e.g. luminescence biosensor or luminescence chemical sensor, according to the invention comprises a multi-layer substrate structure 2 which comprises at least two different types of materials with different binding characteristics for luminophores, e.g. fluorophores. According to the invention, different types of materials also includes two surfaces of a same material which have been submitted to different surface treatments, in that way leading to a kind of different materials, or at least materials with different properties, at least with respect to binding capacity towards luminophores. With binding capacity toward luminophores is meant the ability of a material to bind luminophores, in other words the binding affinity or binding probability of a material toward luminophores. The materials should be such that one material has a first binding capacity for the luminophores and the other material has a second binding capacity for the luminophores, the first binding capacity being higher than the second binding capacity. For example, if the number of luminophores, e.g. fluorophores, binding to the first material is ten times larger than the number of luminophores, e.g. fluorophores, binding to the second material, this may give an improvement which can be as high as one order of magnitude in sensitivity of the luminescence sensor. If the difference between the number of bound luminophores, e.g. fluorophores, on the two materials is higher, the sensitivity may be further improved. Hence, even with a relatively small difference in binding capacity, e.g. a factor of 10, between the first and the second material, a substantial improvement in the sensitivity of the luminescence sensor may be achieved. Preferably, the difference in binding capacity between the first and second material may be as high as possible. Most preferably, the first material shows a high binding capacity toward luminophores while the second material shows substantially no binding capacity toward luminophores.

By using a porous multi-layer substrate structure 2 in accordance with these embodiments of the present invention, it is possible to achieve binding of luminophores, e.g. fluorophores, at specific depths within the porous multilayer substrate structure, e.g. wire-grid. Throughout the description, one example of what is meant by a wire-grid is a substrate comprising slits. The luminescence sensor according to these embodiments of the present invention has an increased sensitivity with respect to prior art luminescence sensors.

In the substrate material an aperture structure comprising at least one aperture such as e.g. at least one hole, gap or any other kind of opening, such as e.g. at least one slit are present. The at least one aperture may have any suitable shape, such as e.g. a square, circular, elliptical, rectangular, polygonal, . . . shape. Moreover, an aperture may extend in two or three dimensions. Therefore, when in the further description is talked about the dimension of an aperture, the smallest dimension of the aperture is to be considered. The substrate may comprise an array of apertures, e.g. holes. The array of apertures may be a periodic array of apertures, e.g. holes, i.e. the distance between the centres of neighbouring apertures may be the same. However, this does not necessarily have to be so. The distance between neighbouring apertures may also be different such that no periodic array is formed.

An aspect of a luminescence sensor according to the present invention is illustrated in cross-section in FIG. 1. An excitation beam 1 is radiating a porous multi-layer substrate structure 2. According to an embodiment of the invention, the porous multi-layer substrate structure 2 comprises at least a first and a second layer of different materials: the first layer comprising a first material with a first binding capacity for luminophores and the second layer comprising a second material with a second binding capacity for luminophores. The first binding capacity may be higher than the second biding capacity or vice versa.

According to the invention, the porous multi-layer substrate structure 2 comprises apertures in which luminophores, e.g. fluorophores, are present and are bound to the surface, mainly to the layer showing the higher binding capacity for luminophores, e.g. fluorophores. The apertures may comprise inner surface walls onto which the luminophores, e.g. fluorophores, may be bound. The inner surface walls, and in particular those of the first material showing a higher binding capacity for luminophores, e.g. fluorophores, may comprise surface immobilized ligands that can recognize one or more targets of interest, also called analyte. This improves the selectivity of the sensor, for example biosensor or chemical sensor. In case more than one analyte has to be detected, the sensor may comprise an array of different ligands. Examples of suitable ligands may be proteins, antibodies, aptamers, peptides, oligonucleotides, sugars, lectins, etc. The ligands may be immobilized to the inner surface walls of the at least one aperture, in particular of the first material showing a high binding capacity for luminophores, e.g. via suitable surface chemistry. The choice of the surface chemistry merely depends on the chemical composition of the inner surface walls.

Upon radiation with the excitation beam 1, the luminophores, e.g. fluorophores, inside the apertures emit luminescence radiation 3, e.g. fluorescent radiation, which leaves the apertures and may be collected by means of a detector 4. According to embodiments of the present invention, the detector 4 may be for example a charge coupled device (CCD) or a complementary metal oxide semiconductor (CMOS) detector. Alternatively, a scanning approach may be used in which only a small imaging view is obtained. Light is collected on a photodiode for a certain time in such a way that an optimal signal to noise ratio may be obtained. This may substantially increase the sensor sensitivity.

Almost no light is transmitted by the aperture structure when the dimensions of the aperture structure are smaller than half the wavelength of the incident radiation, i.e. excitation radiation. In general, in order for the radiation not to enter the apertures, evanescent waves are required, which are waves with spatial frequencies beyond the diffraction limit. This means that for a given wavelength $\lambda$ and refractive index n of the medium that fills the apertures, i.e. e.g. the medium in which the sensor is immersed, the smallest dimension of the apertures should be smaller than $\lambda/(2n)$. Thus, an evanescent field is able to penetrate into the apertures if use is made of an aperture structure comprising apertures with a width smaller than the diffraction limit in the immersion fluid.

Preferably, but not limited hereto, the apertures may have sub-wavelength dimensions, i.e. the apertures in the multilayer substrate structure 2 may have dimensions smaller than the wavelength of the excitation radiation 1, preferably smaller than 50% of the wavelength of the excitation radiation in the medium that fills the apertures, in order to have evanescent wave excitation, more preferred smaller than 40% and most preferred 20% of the wavelength in the medium that fills the apertures. With the medium that fills the apertures is meant the fluid that has to be investigated or in which a target molecule has to be detected. The medium may be a fluid such as a gas or a liquid. In embodiments according to the invention, the fluid may be applied to the apertures by immersing the luminescence sensor in the fluid or by applying the fluid to the apertures by means of e.g. a pipette.

A problem that may arise in a biosensor using a porous substrate having apertures with sub-wavelength width or with a smallest dimension as described in the above embodiments is that the luminescence, e.g. fluorescence, radiation generated within the apertures may be strongly suppressed before it is able to exit the apertures.

Figure 7:
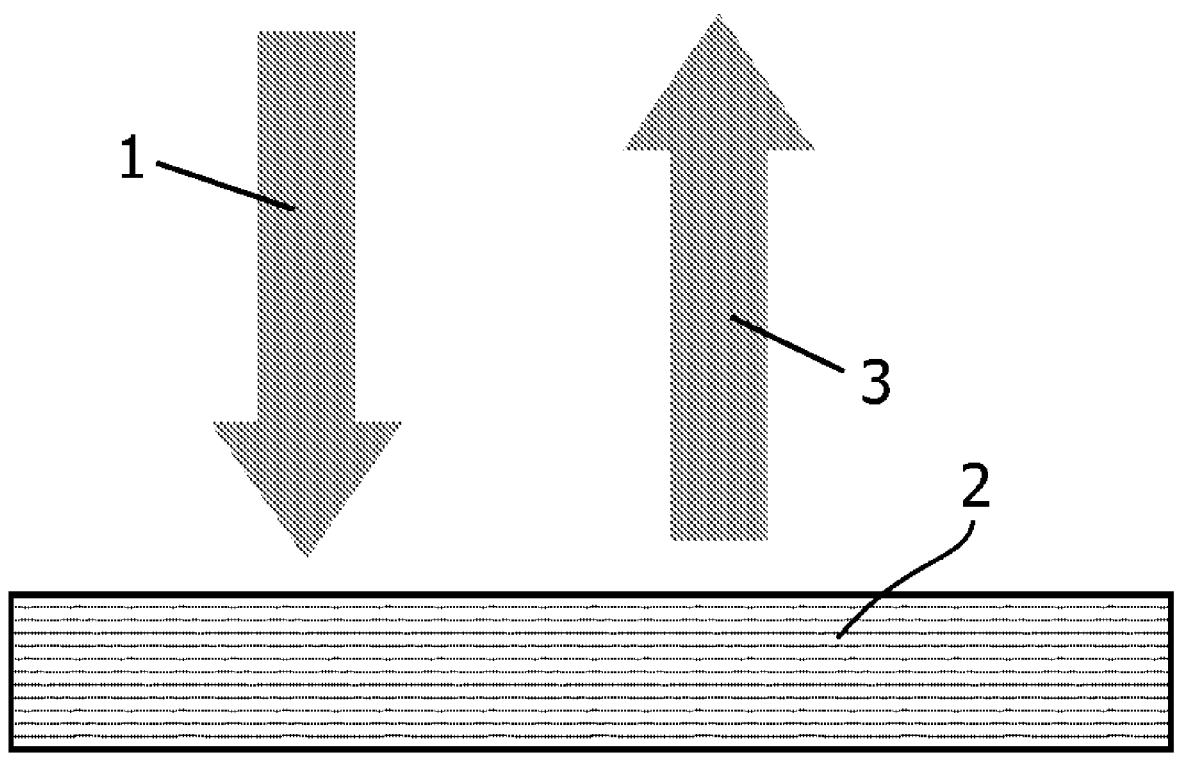
FIG. 7 illustrates the basic principle of a luminescence sensor according to embodiments of the present invention, for use in reflection measurements.

FIG. 1 illustrates an example in which irradiating the luminescence sensor is performed form a first side of the sensor and detecting luminescence radiation is performed from a second side of the sensor, the first and second side being opposite to each other. It has, however, to be understood that this is only an example and that irradiating the sensor with excitation radiation and detecting luminescence radiation coming from the sensor may also be performed at a same side of the sensor, as illustrated in FIG. 7.

Figure 2:
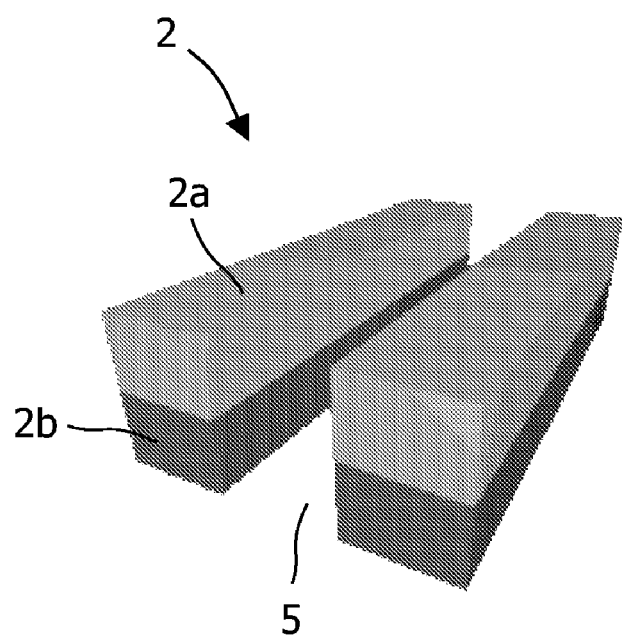
FIG. 2 is a schematic perspective view of a luminescence sensor according to a first embodiment of the invention.

In a first embodiment according to the present invention, the porous multi-layer substrate structure concept is applied to a luminescence sensor, e.g. luminescence biosensor or luminescence chemical sensor, comprising slits 5. FIG. 2 illustrates part of such porous multi-layer substrate structure 2 with slits 5, hence forming a wire grid, of a luminescence sensor according to the first embodiment of the invention. The porous multi-layer substrate structure 2 illustrated comprises a first layer 2a comprising a first material with a first binding capacity toward luminophores, e.g. fluorophores, and a second layer 2b comprising a second material with a second binding capacity toward luminophores, e.g. fluorophores, the second binding capacity being lower than the first binding capacity. The multi-layer substrate structure 2 is formed as follows. First, a first layer 2a is provided, formed of a first material that has a first binding capacity toward luminophores, e.g. fluorophores. Then, a second layer 2b is formed onto the first layer, the second layer being formed of a second material that has a second binding capacity toward luminophores, e.g. fluorophores. This may be performed by any suitable deposition technique known by persons skilled in the art. According to the invention, the first binding capacity is higher than the second binding capacity or vice versa. Preferably, the difference in binding capacity between the first and second layer may be at least a factor ten, more preferred as high as possible. Most preferably, the first material shows a high binding capacity toward luminophores, e.g. fluorophores, while the second material shows substantially no binding capacity toward luminophores, e.g. fluorophores, or vice versa. In a next step, at least one slit 5 may be provided through the multi-layer substrate structure 2, i.e. through the first layer 2a and through the second layer 2b. This may be done by any suitable conventional technique known by persons skilled in the art, such as for example etching.

In this embodiment it is assumed that the excitation beam 1 (not illustrated in FIG. 2 but shown in FIG. 1) comes from above the porous multi-layer substrate structure 2. In that case the preferred binding site for luminophores, e.g. fluorophores is at that side of the porous multi-layer substrate structure 2 where excitation radiation 1 takes place, thus at the top side of the porous multi-layer substrate structure 2 in the example given, where the material is positioned with the highest binding capacity toward luminophores, e.g. fluorophores. However, in case the excitation beam 1 comes from under the porous multi-layer substrate structure 2, the first layer 2a with the first, higher binding capacity toward luminophores, e.g. fluorophores, is preferably positioned under the second layer 2b with the second, lower binding capacity toward luminophores, e.g. fluorophores, i.e. in the opposite configuration than illustrated in FIG. 2.

As already mentioned before, in the example given in FIG. 2, the first layer 2a may comprise a material that has a first, higher binding capacity for luminophores, e.g. fluorophores. The second layer 2b may then comprise a material that has a second, lower binding capacity for luminophores, e.g. fluorophores. In that way, luminophores, e.g. fluorophores, preferably bind to the upper half of the multi-layer structure 2, i.e. to the first layer 2a comprising the material which shows a higher binding capacity toward the luminophores, e.g. fluorophores.

In the example given in FIG. 2 for transmission measurement, a slit 5 is irradiated from the top and the detector collects the luminescence radiation, e.g. fluorescence radiation, at the bottom of the multi-layer substrate structure 2. As the excitation radiation is suppressed by the slit 5, the highest excitation intensity is at the top of the slit 5. However, luminescence radiation generated at the top of the slit 5 is substantially suppressed before it reaches the bottom of the slit 5, where the detector is positioned.

Figure 3:
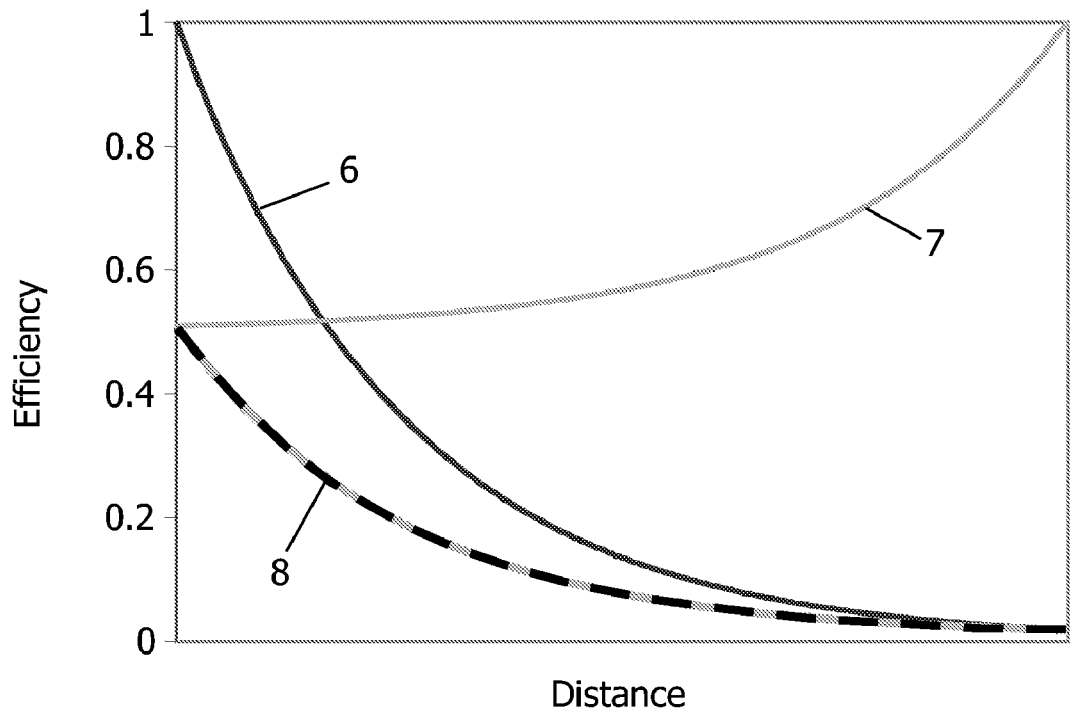
FIG. 3 illustrates the combined effect of excitation radiation and detection of luminescence radiation.

FIG. 3 illustrates the combined effect of excitation efficiency and luminescence detection efficiency for the wire grid sensor as illustrated in FIGS. 1 and 2 where the sensor is irradiated from the top and the detector collects the luminescence radiation, e.g. fluorescence radiation, at the bottom of the multi-layer substrate structure 2. As can be seen from FIG. 3, the excitation efficiency (the graph indicated by reference number 6) is highest at the entrance of the slit 5 (at the left of the x-axis). Furthermore, it can be seen that the luminescence detection efficiency (the graph indicated by reference number 7) is always higher than 50% and is highest at the exit of the slit 5 (at the right of the x-axis). Locations where the luminophores, e.g. fluorophores, preferably bind can be found by multiplying the effect of the excitation efficiency (curve 6) and the luminescence detection efficiency (curve 7), which is illustrated by the combined efficiency curve (indicated by reference number 8 in FIG. 3). The combined efficiency curve 8 is slightly lower but similar to the excitation efficiency curve 6.

The combined efficiency of excitation and luminescence detection thus gives information about whether a luminophore, e.g. fluorophore, is excited efficiently, combined with the question whether the generated luminescence can reach the detector efficiently. Due to this effect there will be locations in the slits 5 where the combined efficiency is highest and therefore the luminophores, e.g. fluorophores, should preferably bind at these locations. As, in the example given, the combined efficiency is highest at the entrance of the slit 5, the luminophores, e.g. fluorophores, preferably bind to this location. Thus, in the example given in FIG. 2, the efficiency with which the luminescence radiation is detected is the highest at the entrance of the slit 5 and thus nearest to the excitation radiation source.

Figure 4:
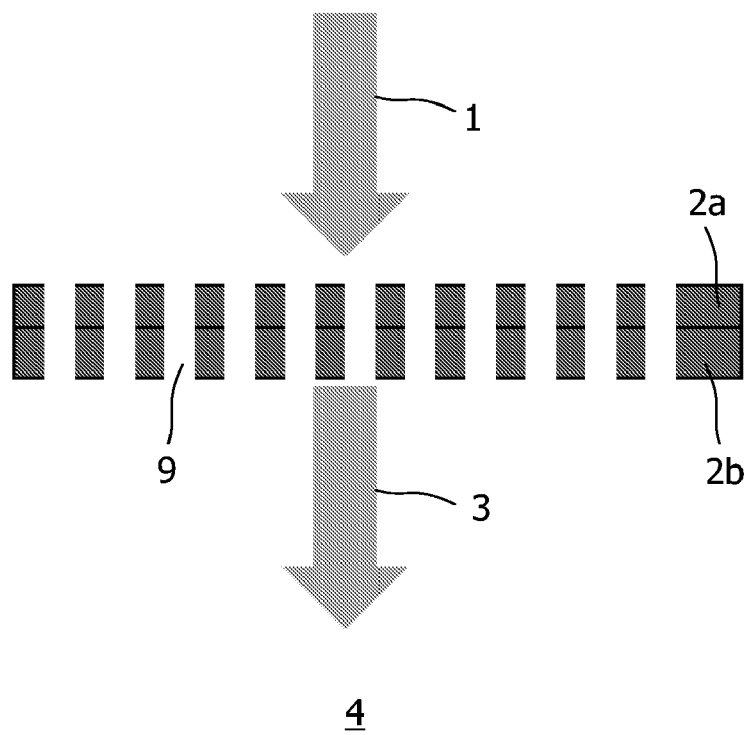
FIG. 4 illustrates the basic principle of a first implementation of a luminescence sensor according to a second embodiment of the invention.
Figure 5:
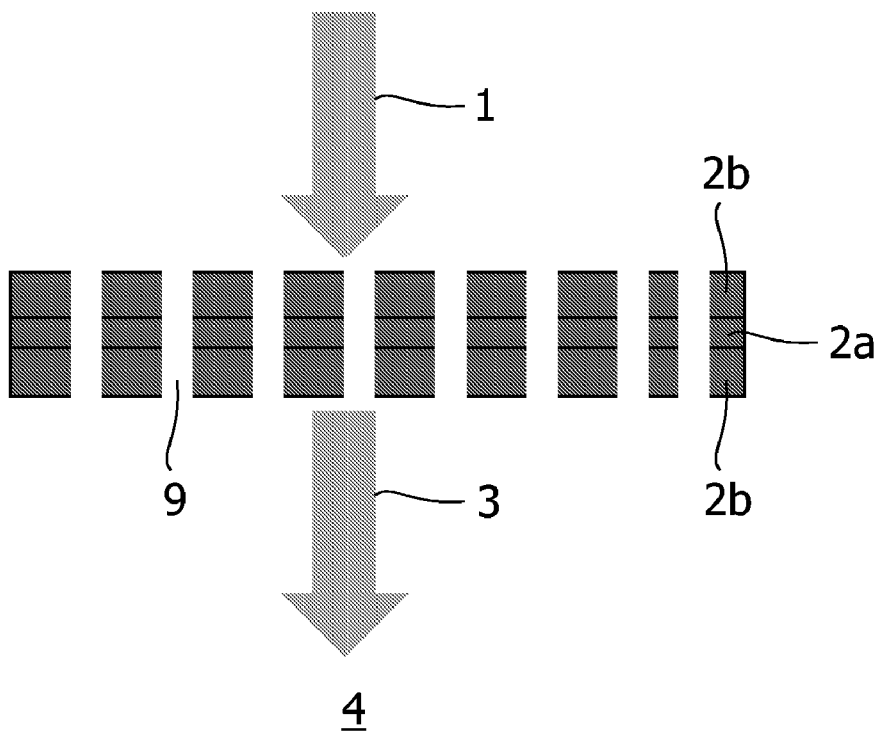
FIG. 5 illustrates the basic principle of a second implementation of a luminescence sensor according to the second embodiment of the invention.

In a second embodiment according to the present invention, the multi-layer substrate structure concept is applied to a sensor, e.g. a biosensor, comprising apertures 9, such as e.g. pinholes, instead of the slits 5 as in the first embodiment of the present invention. For a luminescence sensor, e.g. a luminescence biosensor, comprising apertures 9, such as e.g. pinholes, the preferred binding site for luminophores, e.g. fluorophores, depends on the balance between the suppression of excitation radiation 1 and the suppression of luminescence radiation 3, e.g. fluorescence radiation. Therefore it is difficult to determine where the preferred binding sites for the luminophores, e.g. fluorophores, are, but typically the multi-layer structure 2 may be such that the binding material is either at the top of the apertures 9 and thus at the side of the excitation radiation 1 (see FIG. 4) or somewhere halfway (see FIG. 5). In that case, the multi-layer structure 2 may for example comprise three layers, i.e. a layer 2a of material that has a first binding capacity for luminophores, e.g. fluorophores, sandwiched in between two layers 2b of material that has a second binding capacity for the luminophores, e.g. fluorophores, the second binding capacity being lower than the first binding capacity. The two layers 2b may, according to embodiments of the invention and as is the case in the example given in FIG. 5, both have the same thickness. However, in other embodiments according to the invention, the two layers 2b may have a different thickness.

The multi-layer substrate structure 2 according to the second embodiment may be formed in a similar way as described for the multi-layer structure 2 according to the first embodiment. For the multi-layer substrate structure 2 illustrated in FIG. 4, the difference with the method described in the first embodiment is that now, instead of slits 5, pinholes 9 have to be provided through the multi-layer structure 2. For the multi-layer substrate structure 2 illustrated in FIG. 5, a first layer 2a is provided with a first material showing a first binding capacity toward luminophores, e.g. fluorophores. Then, a second layer 2b of a second material that shows a second binding capacity toward luminophores, e.g. fluorophores, the second binding capacity being lower than the first binding capacity, is provided at a first side and at a second side, opposite to the first side, of the first layer 2a. In a next step, pinholes 9 are provided through the first layer 2a and through the second layers 2b.

Figure 6:
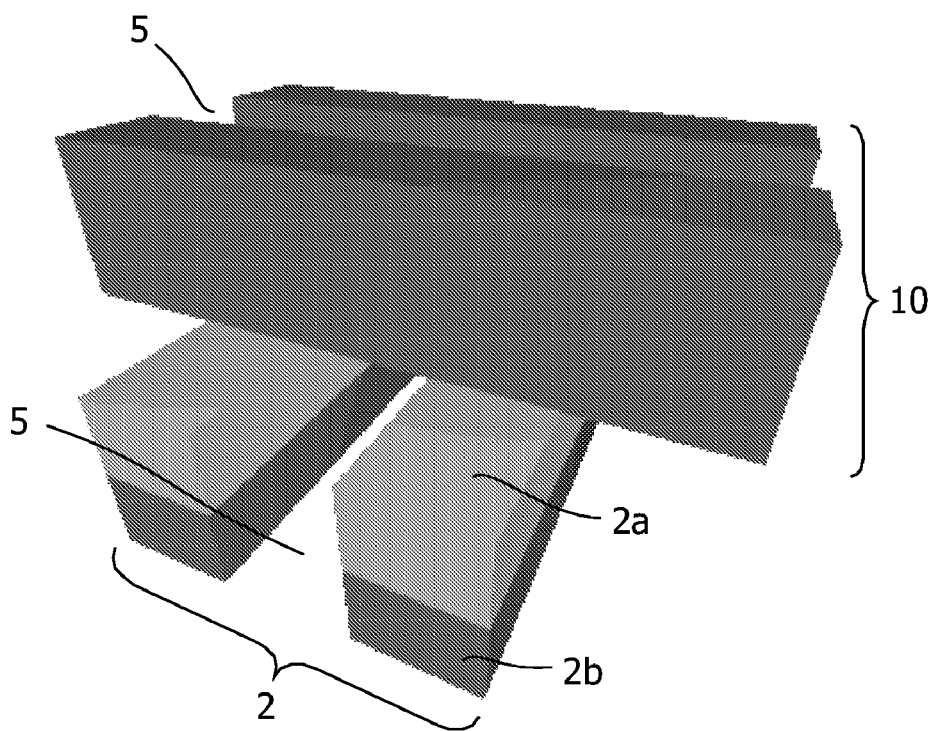
FIG. 6 is a schematic perspective view of a luminescence sensor according to the first embodiment of the invention.

In a third embodiment of the present invention, a multi-layer wire grid 2 as described in the first embodiment according to this invention is used as a substrate to form a double wire-grid sensor. With wire grid is meant a substrate having slits 5 in it. In this embodiment, the luminescence sensor may comprise a bottom wire grid 2 and a top wire grid 10. The bottom wire grid 2 may comprise at least a first layer 2a and a second layer 2b. In the example illustrated in FIG. 6 the upper part, in the example given the first layer 2a, of the bottom wire grid 2, may comprise a first material that shows high binding capacity toward luminophores, e.g. fluorophores, and the second layer 2b may comprise a second material which shows substantially no binding capacity toward luminophores, e.g. fluorophores. On top of the bottom wire grid 2 a top wire grid 10 is positioned which is formed out of a material that shows substantially no binding capacity toward luminophores, e.g. fluorophores. The material the top wire grid 10 is formed of may be the same as the material of the second layer 2b. However, in other embodiments according to the invention, the material the top wire grid 10 is formed of may also be another material that shows no binding capacity toward the luminophores, e.g. fluorophores. The top wire grid 10 may be positioned such that its slits 5 are lying in a plane substantially parallel to the plane in which the slits 5 of the bottom wire grid 2 are positioned while running in a direction substantially perpendicular to the direction in which the slits 5 of the bottom wire grid 2 are running.

The multi-layer structure 2 of the sensor according to the third embodiment may be formed in a same way as described in the first embodiment. In this embodiment, however, furthermore a top wire grid 10 may be provided on top of the multi-layer substrate structure 2. This may be done by providing a layer of suitable material for forming the top wire grid 10 onto the multi-layer substrate structure 2 by any suitable technique and by subsequently providing slits 5 in the layer in order to form the top wire grid 10.

In the above-described embodiments, it is assumed that detection is performed in transmission mode. This means that the sensor is irradiated with excitation radiation, e.g. excitation light, from a first side of the sensor and that luminescence radiation, e.g. fluorescent radiation, is detected at a second side of the sensor which is opposite to the first side.

However, according to other, though less preferred, embodiments of the invention, the invention also applies for detection in reflection mode. This means that the multi-layer structure 2 of the sensor according to the invention may also be irradiated with excitation radiation 1, e.g. excitation light, from a first side of the sensor and that detection of luminescence radiation 3, e.g. fluorescence radiation, may be performed at that same first side of the sensor. This is illustrated in FIG. 7.

An advantage of detection in reflection mode, with respect to detection in transmission mode, is that more luminescence radiation 3, e.g. excitation radiation, will be able to reach the detector 4 as it does not have to go all the way through the slits 5 or apertures 6. Similar to detection in transmission mode, preferred binding sites for luminophores, e.g. fluorophores, may be at the top of the multi-layer structure 2, i.e. at the entrance of the slit 5 or aperture 6. This can also be seen from FIG. 3. The effect of combined efficiency for a multi-layer sensor in reflection mode is similar to the effect for a multi-layer sensor in transmission mode as is illustrated in FIG. 3.

However, a disadvantage of the reflection mode and the reason why it is less preferred than the transmission mode is that excitation radiation 1 and luminescence radiation 3 are not separated while, in case of sub-wavelength slits 5 or apertures 6, excitation radiation 1 and luminescence radiation 3 are separated when detection is performed in transmission mode. Hence, when detection is performed in reflection mode, a filter, such as e.g. an interference filter, may be required.

According to embodiments of the present invention, binding and non-binding materials, necessary for forming the first layer 2a and the second layer 2b of the multi-layer substrate structure 2 may be achieved in various ways:

For, for example, DNA, which has a negative charge, if the material has a positive charge, this charge will induce a force on the DNA that will pull the DNA towards the material, increasing the chance for the molecule to bind to the surface of the material. Hence, it will give preferred binding so it can be used to form the layer 2a which shows a higher binding activity toward luminophores, e.g. fluorophores. Likewise, if the material has a negative charge, the charge will induce a force on the DNA that is directed away from the material and therefore it is not likely that DNA will bind to this material. Hence, a negatively charged material can prevent binding of DNA to the material and hence, such materials may be used to form layer 2b that shows a lower binding capacity toward luminophores, e.g. fluorophores.

Instead of using the 'natural' charge of a material it is possible to charge the materials with an electrical voltage. In order to achieve this, an electrically conducting layer of material may be inserted between the binding or first layers comprising a first material and the non-binding or second layers comprising a second material. This allows a positive charge to be on the first material or binding material, with a negative charge on the second or non-binding material. Suitable materials should be conductive, therefore, examples of materials that can be used here are e.g. semiconductors or metals.

It is also possible to achieve preferred binding with chemical reactions. For example, some materials oxidize easily, while others barely oxidize. This effect may be used to achieve preferred binding for one of these materials.

Suitable materials for binding several kinds of biomolecules are described in "Diagnostic Biosensor Polymers", Ed. A. M. Asmani and N. Akmal, American Chemical Society, 1994.

According to a further embodiment of the invention, the multi-layer substrate structure 2 as described in the above embodiments, may comprise at least one layer with a chemical composition such that, when the luminescence sensor is in contact with a fluid to be examined, no reaction takes place between the luminescence sensor and the fluid the sensor is in contact with.

Preferably, the multi-layer substrate structure 2 may comprise at least one first layer 2a and at least one second layer 2b as described in the above embodiments and on top of this multi-layer structure 2 at least one layer may be positioned with a chemical structure such that no reaction takes place between this at least one layer and the fluid that is provided to the sensor.

In other embodiments, the multi-layer substrate structure 2 may comprise at least one first layer 2a and at least one second layer 2b as described in the above embodiments and one of the at least one first layer 2a, which is at that side of the sensor at which the fluid to be examined is provided, may have a chemical structure such that substantially no reaction takes place between that layer and the fluid that is provided.

It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. A luminescence sensor, the sensor comprising a first porous multi-layer substrate structure (2) with apertures (5, 9), the multi-layer substrate structure (2) comprising at least one first layer (2a) formed of a first material and at least one second layer (2b) formed of a second material, wherein the first material shows a first binding capacity towards luminophores present in the apertures (5, 9) and the second material shows a second binding capacity towards luminophores present in the apertures (5, 9), the second binding capacity being lower than the first binding capacity.

2. A luminescence sensor according to claim 1, wherein the multi-layer substrate structure (2) comprises slits (5) and one first layer (2a) and one second layer (2b).

3. A luminescence sensor according to claim 2, wherein the first layer (2a) is positioned on top of the second layer (2b) and is closest to a side of the sensor where an excitation radiation source is positioned for irradiating the sensor.

4. A luminescence sensor according to claim 1, wherein the multi-layer substrate structure (2) comprises pinholes (9) and one first layer (2a) and one second layer (2b).

5. A luminescence sensor according to claim 4, wherein the first layer (2a) is positioned on top of the second layer (2b) and is closest to a side of the sensor where an excitation radiation source is positioned for irradiating the sensor.

6. A luminescence sensor according to claim 4, wherein the multi-layer substrate structure (2) comprises a further second layer (2b), wherein the first layer (2a) is sandwiched in between the second layer (2b) and the further second layer (2b).

7. A luminescence sensor according to claim 1, wherein the sensor furthermore comprises a second substrate structure (10) formed of a material which shows substantially no binding capacity towards luminophores, which second multi-layer substrate structure (10) is positioned on top of the first multi-layer substrate structure (2).

8. A luminescence sensor according to claim 7, the first multi-layer substrate structure (2) lying in a first plane and having slits (5) running in a first direction and the second substrate structure (10) lying in a second plane and having slits (5) running in the second direction, wherein the first plane is substantially parallel to the second plane and wherein the first direction is substantially perpendicular to the second direction.

9. A luminescence sensor according to claim 1, wherein the apertures (5, 9) have sub-wavelength dimensions.

10. A luminescence sensor according to claim 1, the sensor furthermore comprising an excitation radiation source for irradiating the sensor and a detector (4) for detecting luminescence radiation, wherein said excitation radiation source is positioned at a first side of the sensor and said detector (4) is positioned at a second side of the sensor, the first and second side being opposite to each other.

11. A luminescence sensor according to claim 1, the sensor furthermore comprising an excitation radiation source for irradiating the sensor and a detector (4) for detecting luminescence radiation, wherein said excitation radiation source and said detector (4) are positioned at a same side of the sensor.

12. A luminescence sensor according to claim 1, comprising at least one layer with a chemical composition such that, when the luminescence sensor is in contact with a fluid to be examined, no reaction takes place between the luminescence sensor and the fluid the sensor is in contact with.

13. A method for the manufacturing of a luminescence sensor for the detection of luminophores, the sensor comprising a first multi-layer substrate structure (2), the method comprising:

provinding at least one first layer (2a) formed of a first material that shows a first binding capacity towards luminophores, providing on the at least one first layer (2a) at least one second layer (2b) formed of a second material that shows a second binding capacity, lower than the first binding capacity, towards luminophores, and providing at least one aperture (5, 9) through the at least one first layer (2a) and the at least one second layer (2b).

14. A method according to claim 13, wherein providing at least one first layer (2a) and providing at least one second layer (2b) comprises providing a first layer (2a) and two second layers (2b) such that the first layer (2a) is sandwiched in between the two second layers (2b).

15. A method according to claim 13, the first multi-layer substrate structure (2) comprising slits (5) lying in a first plane and running in a first direction, wherein the method furthermore comprises providing on top of the first multi-layer substrate structure (2), a second substrate structure (10) lying in a second plane and having slits (5) running in a second direction, such that the first plane is substantially parallel with the second plane and the first direction is substantially perpendicular to the second direction.

16. A luminescence sensor according to claim 1, wherein the sensor is a luminescence biosensor.

17. A luminescence sensor according to claim 16, wherein the luminescence biosensor is a fluorescence biosensor.

* * * * *